(12) United States Patent
Crespi et al.

(10) Patent No.: US 7,879,607 B2
(45) Date of Patent: Feb. 1, 2011

(54) ELASTOMERIC DEVICE FOR CELL SEEDING ON THE BOTTOM OF A FILTER

(75) Inventors: Charles L. Crespi, Marblehead, MA (US); Xiaoxi (Kevin) Chen, Westborough, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 545 days.

(21) Appl. No.: 11/750,067

(22) Filed: May 17, 2007

(65) Prior Publication Data

US 2007/0269850 A1 Nov. 22, 2007

Related U.S. Application Data

(60) Provisional application No. 60/747,696, filed on May 19, 2006.

(51) Int. Cl.
*C12N 5/00* (2006.01)
*C12N 5/02* (2006.01)
*B01L 99/00* (2010.01)
*G01N 1/18* (2006.01)

(52) U.S. Cl. .................. 435/395; 435/401; 435/373; 422/101; 436/177

(58) Field of Classification Search ............... 422/99
See application file for complete search history.

(56) References Cited

U.S. PATENT DOCUMENTS 5,272,083 A * 12/1993 Butz et al. ............ 435/401
5,468,638 A * 11/1995 Barker et al. ............ 435/304.1
5,470,743 A    11/1995 Mussi et al.
5,665,596 A *  9/1997 Mussi ..................... 435/373
2003/0073228 A1* 4/2003 Duffy et al. ............. 435/287.1

FOREIGN PATENT DOCUMENTS

| DE | 101 17 723 A1 | 10/2002 |
| EP | 0 735 134 A2 | 10/1996 |
| EP | 0 757 097 A2 | 2/1997 |

OTHER PUBLICATIONS

English translation of DE 10117723 (Machine translation).*

* cited by examiner

*Primary Examiner*—Jill Warden
*Assistant Examiner*—Charles Hammond
(74) *Attorney, Agent, or Firm*—Hoffmann & Baron, LLP

(57) ABSTRACT

An article is provided herein for use in seeding cells on at least one filter extending across at least one well of an assay device. The article includes an elastomeric body having spaced-apart first and second surfaces, and at least one channel extending between, and through, the first and second surfaces. The channel is formed to sealingly, and detachably, engage an outer surface of the well with the filter being at least partially encompassed by the channel. Advantageously, with the subject invention, a cell monolayer can be formed on the exterior surface of the filter. The assay device may be a multiwell plate, an insert plate, a column, a test tube, or a pipette.

12 Claims, 3 Drawing Sheets

ELASTOMERIC DEVICE FOR CELL SEEDING ON THE BOTTOM OF A FILTER

CROSS-REFERENCE TO RELATED APPLICATION

This application claims priority of U.S. Provisional Patent Appl. No. 60/747,696, filed May 19, 2006, the contents of which are incorporated by reference herein in its entirety.

FIELD OF THE INVENTION

The subject invention is directed to articles and methods for use in seeding cells on filters of assay devices.

BACKGROUND OF THE INVENTION

Drug permeability screening assays are known, in the prior art. With reference to FIG. 1, a typical arrangement for conducting such assays is depicted. A multiwell insert plate 10 is shown having a plurality of open wells 12 with a porous membrane or filter 14 extending across a bottom end of each of the wells 12. The filter 14 is typically of polyvinylidene difluoride (PVDF), polyethylene terephthalate (PET) or a polycarbonate (PC) material. A corresponding receiver plate 16 is also shown having closed-bottom receiver wells 18. In use, buffered solutions containing compounds to be analyzed are disposed into the receiver wells 18. Buffered solutions without the compounds of interest are disposed into the wells 12 of the insert plate 10, and the insert plate 10 is placed atop the receiver plate 16 with the filters 14 coming into contact with the buffered solutions of compounds contained in the receiver wells 18. The concentrations of the compounds in the solutions of both the insert plate 10 and the receiver plate 16 are analyzed to observe the diffusion of the compounds through the filters 14 and to determine the compounds' permeabilities.

Under certain circurmstances (e.g., certain assays), it may be desirable to have one or more cell monolayers formed on the filters. With reference to FIG. 2, it is known in the art to dispose a cell media solution into the wells 12 of the insert plate to incubate cells on the respective interior surfaces of the filters 14 and to form cell monolayers thereon. However, greater difficulty exists in forming cell monolayers on the exterior surfaces of the filters. As shown in FIG. 3, a technique has been developed where the insert plate 10 is inverted and a drop of cell media solution is disposed onto each of the filters 14. Because a limited volume of the cell media may be disposed onto each of the filters 14, it is difficult to consistently achieve a tight cell monolayer, which requires high cell density and long incubation time. The failure to form a tight cell monolayer may lead to "holes" in the cell monolayer and possible failure in the drug permeability screening assays.

Formation of cell monolayers on the exterior surfaces of the filter membranes is desired for several reasons. First with cell monolayers on both sides of the filter membranes, particularly of different types of cells, cell communications can be studied. Second, the exterior surface monolayers permit researchers to conduct polarized drug transport studies in a manner which permits the use of identical buffer solution configurations for each direction of drug transport (apical to basolateral and basolateral to apical).

SUMMARY OF THE INVENTION

An article is provided herein for use in seeding cells on at least one filter extending across at least one well of an assay device. The article includes an elastomeric body having spaced-apart first and second surfaces, and at least one channel extending between, and through, the first and second surfaces. The channel is formed to sealingly, and detachably, engage an outer surface of the well with the filter being at least partially encompassed by the channel. Advantageously, with the subject invention, a cell monolayer can be formed on the exterior surface of the filter. The assay device may be a multiwell plate, an insert plate, a column, a test tube, or a pipette.

In a further aspect of the subject invention, a method is provided for seeding cells on at least one filter extending across at least one well of an assay device. The method includes providing a body having spaced-apart first and second surfaces, and at least one channel extending between, and though, the first and second surfaces; and, disposing the body onto the well with the channel sealingly engaging the well and the filter being at least partially encompassed by the channel.

These and other features of the subject invention will be better understood through a study of the following detailed description and accompanying drawings,

DETAILED DESCRIPTION OF THE INVENTION

Figure 1:
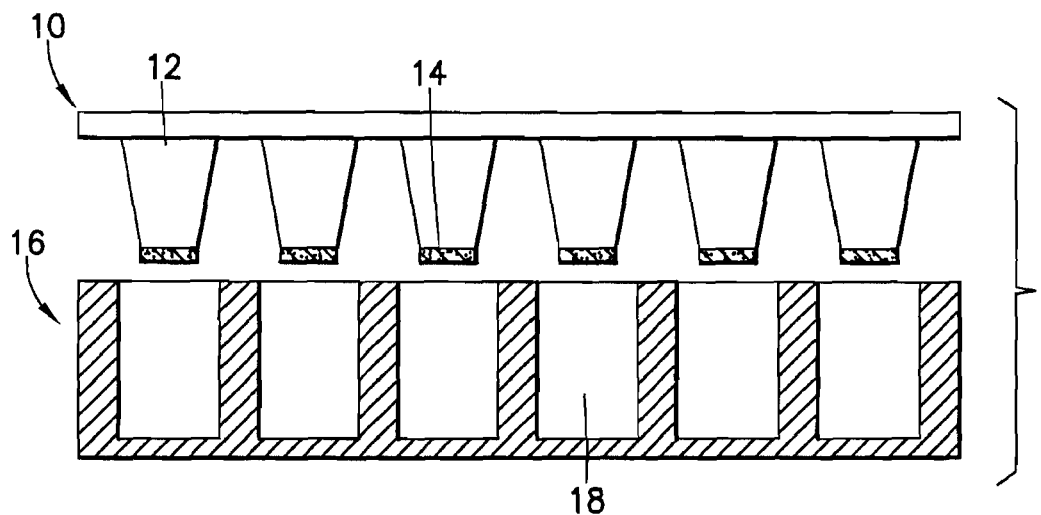
FIG. 1 shows an arrangement of an insert plate and a receiver plate.
Figure 2:
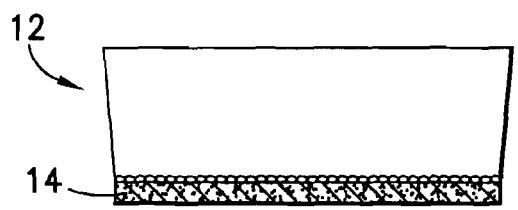
FIG. 2 shows schematically a cell monolayer formed on an interior surface of a filter.
Figure 3:
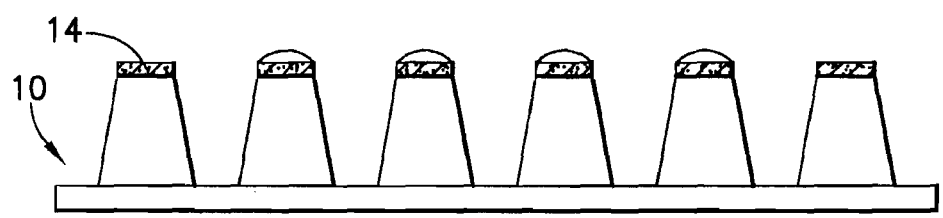
FIG. 3 shows a prior art method for seeding cells on the exterior surfaces of filters.
Figure 4:
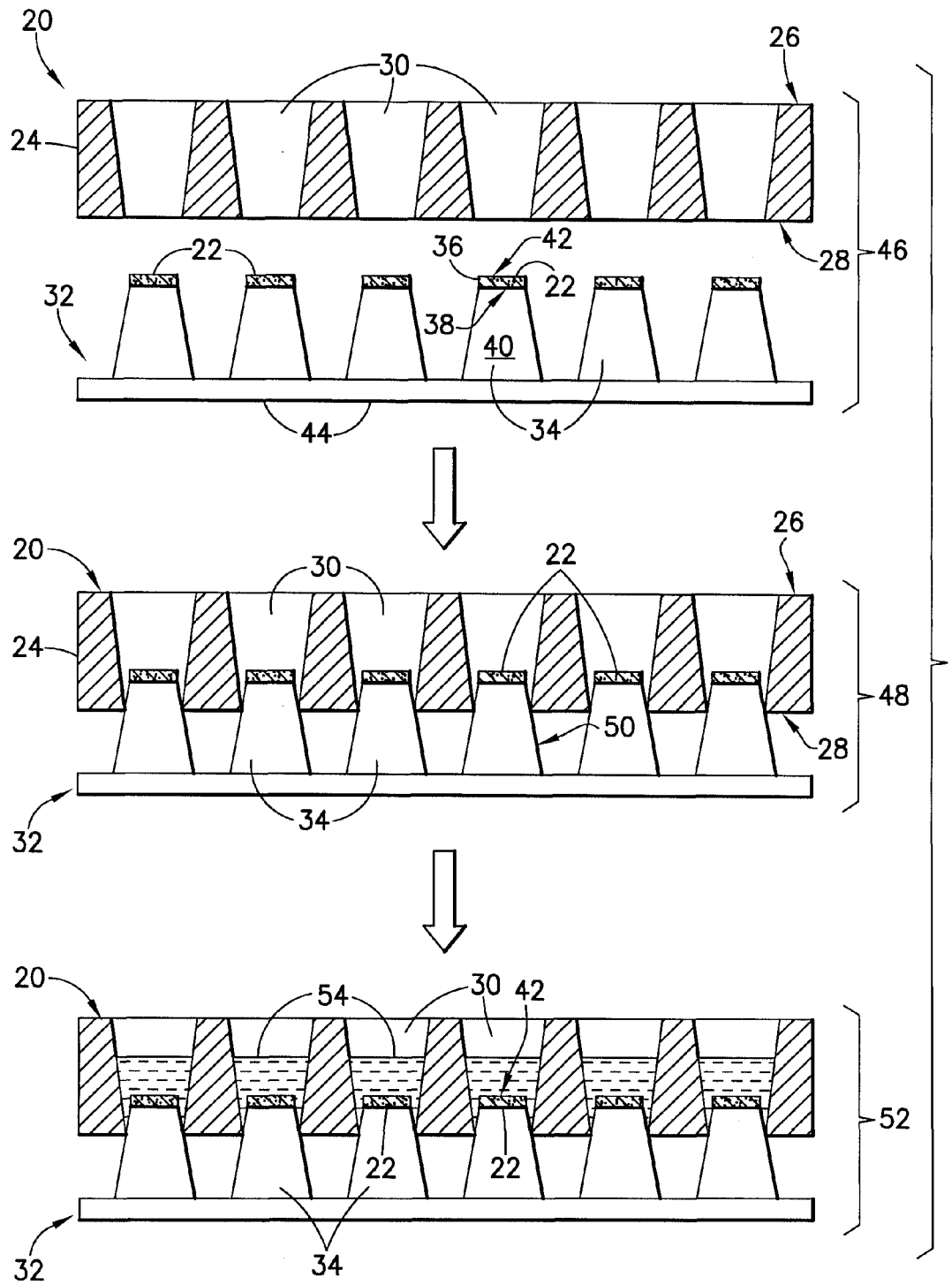
FIG. 4 shows an article formed in accordance with the subject invention in use with an assay device in the form of an insert plate.

With reference to FIG. 4, an article 20 is provided for use in seeding cells on one or more membranes or filters 22. The article 20 includes a body 24, which is preferably unitary, and spaced-apart first and second surfaces 26 and 28, which are preferably formed to be parallel to one another. One or more channels 30 are formed to extend between, and through, the first and second surfaces 26, 28. The body 24 may be formed of varying dimensions with various quantities of the channels 30 being provided and being arranged in various arrays.

The cross-sections of the channels 30 may be constant or may be variable throughout the lengths thereof Preferably, as shown in FIG. 4, the channels 30 are formed with tapered configurations which converge towards the second surface 28. The cross-sections of the channels 30 will be formed to define fluid-tight seals with corresponding wells of an assay device as described below.

It is preferred that the body 24 be formed of an elastomeric material. More preferably, the body 24 is formed from polydimethylsiloxane (PDMS). PDMS allows for tight sealing and easy, non-destructive removal after use.

The filters 22 may be formed of any known material including PVDF, PET or a polycarbonate (PC) material. Also, the filters 22 may be of different thicknesses and include pores of various dimensions and configurations.

The article 20 may be used in various applications, but is particularly well-suited for use in conjunction with an assay device 32. The assay device 32 may be any device used in assay or test procedures (e.g., drug permeability screening assays), including, but not limited to, multiwell plates, insert plates, columns, test tubes, and pipettes. For illustrative purposes, the assay device 32 is shown and described as an insert plate, but other configurations are possible. The assay device 32 includes at least one well 34 across which the filter 22 extends. Preferably, the well 34 terminates at an open end 36 across which the filter 22 extends. The filter 22 may be affixed to the well 34 using various techniques, including, by way of non-limiting examples, bonding, fusion and mechanical fixation. An interior surface 38 of the filter 22 faces an interior 40 of the well 34, while exterior surface 42 of the filter 22 faces away from the interior 40. The assay device 32 may include a plurality of the wells 34 with each having one or more of the filters 22. Preferably, the wells 34 each include an open receiving end 44, opposite the open end 36, formed to receive assay solutions (e.g., buffer solution(s)) into the respective well 34.

It is preferred that the article 20 be provided with the number and locations of the channels 30 corresponding to the number and the locations of the wells 34 on the assay device 32. In this manner, the article 20 can be used to simultaneously seed cells on a plurality of the filters 22. In addition, the channels 30, particularly at the second surface 28, are each formed to define a fluid-tight seal on the wells 34 with the filters 22 being at least partially encompassed by the channels 30. Specifically, at least the exterior surfaces 42 of the filters 22 are to be encompassed by the channels 30; however, it is preferred that the filters 22 be wholly encompassed by the channels 30.

With reference to FIG. 4, use of the article 20 is depicted. It is preferred that in a first step 46, the assay device 32 be positioned to have the exterior surfaces 42 of the filters 22 be facing gravitationally upwardly (e.g., by inverting the assay device 32). In a second step 48, the body 24 is disposed onto the assay device 32 with the channels 30 sealingly engaging the wells 34 with the filters 22 being at least partially encompassed by the channels 30. The channels 30 form fluid-tight seals on outer surfaces 50 of the wells 34. Preferably, the channels 30 sealingly engage the outer surfaces 50 at locations spaced from the filters 22 with the filters 22 being at least partially encompassed by the channels 30. With the channels 30 having a tapered configuration, it is preferred that the wells 34 be inserted into the channels 30 through the second surface 28, which defines narrower openings in the channels 30 than the first surface 26.

In a third step 52, one or more cell media solutions 54 are disposed into each of the channels 30 above the filters 22. With the fluid-tight seals defined by the channels 30, and the at least partial encompassing of the filters 22 by the channels 30, the cell media solutions 54 are retained within the channels 30 in communication with the filters 22. It is preferred that cell incubation be allowed so as to facilitate formation of cell growth on the exterior surfaces 42 of the filters 22. Once prepared, the cell media solutions 54 are removed and the article 20 is detached, leaving the assay device 32 ready for use.

Figure 5:
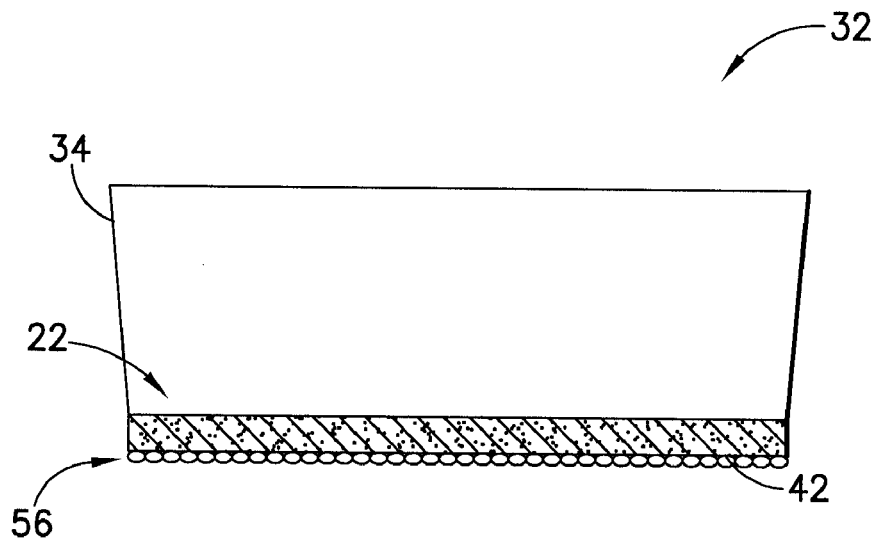
FIG. 5 shows schematically a cell monolayer formed on an exterior surface of a filter; and, FIG. 6 shows schematically cell monolayers formed on interior and exterior surfaces of a filter.

As shown in FIG. 5, a cell monolayer 56 can be developed on the exterior surface 42 of one or more of the filters 22 using the present invention. For each of the filters 22, the cell monolayer 56 can be tightly formed due to the ability to maintain the cell media solutions 54 in sufficiently large quantities across the exterior surface 42 of the entire expanse of the filter 22.

Figure 6:
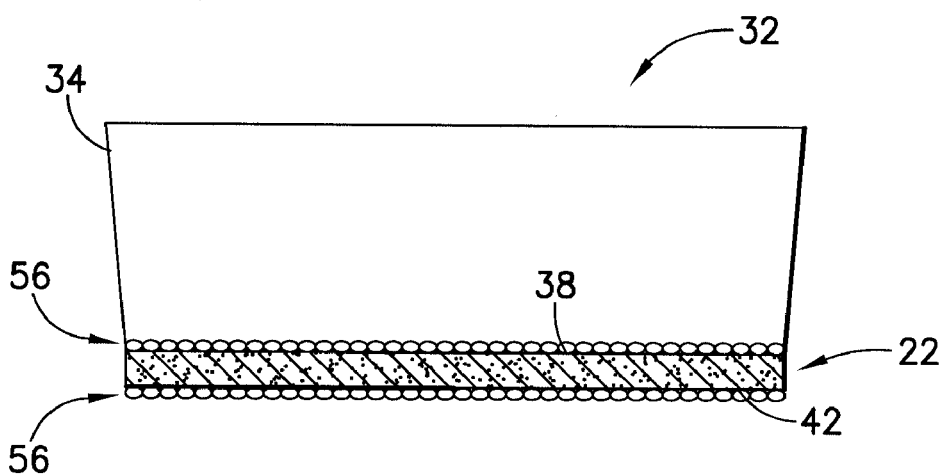

The subject invention can be used with conventional methodology. For example, with reference to FIG. 6, Known techniques for seeding cells can be used to develop the cell monolayer 56 on the Interior surface 38 of one or more of the filters 22. Also, the subject invention can be used to develop the cell monolayer 56 on the exterior surface 42 of one or more of the filters 22 to have the filter(s) 22 sandwiched by the cell monolayers 56. The cell monolayers 56 can be formed of the same or of different types of cells to permit the study of cell communications.

What is claimed is:

1. A method for seeding cells on at least one filter extending across at least one well of an assay device, said method comprising:
    providing an assay device with at least one well with at least one filter extending across said at least one well;
    providing a body having spaced-apart first and second surfaces, and at least one channel extending between, and through, said first and second surfaces; and,
    disposing said body onto said well with said channel sealingly engaging said well at a location spaced from said filter and said filter being at least partially encompassed by said channel,
    wherein said channel is tapered so as to converge from said first surface to said second surface, said well extending into said channel through said second surface with said body being disposed on said well.

2. A method as in claim 1, wherein said filter includes an interior surface facing the interior of said well and an exterior surface facing away from the interior of said well, said exterior surface of said filter being encompassed by said channel.

3. A method as in claim 2, further comprising the step of directing said exterior surface of said filter to face gravitationally upwardly before the step of disposing said body onto said well.

4. A method as in claim 3, further comprising the step of seeding cells on said interior surface of said filter.

5. A method as in claim 2, further comprising the step of seeding cells on said interior surface of said filter.

6. A method as in claim 1, wherein said body is elastomeric.

7. A method as in claim 1, wherein said body is formed from polydimethylsiloxane.

8. A method as in claim 1, further comprising the step of disposing at least one cell media solution in said channel after the step of disposing said body onto said well.

9. A method as in claim 8, further comprising the step of allowing cell incubation after the step of disposing at least one cell media solution in said channel.

10. A method as in claim 9, further comprising the step of detaching said body from said well after the step of allowing cell incubation.

11. A method as in claim 8, further comprising the step of detaching said body from said well after the step of disposing at least one cell media solution in said channel.

12. A method as in claim 1, wherein said assay device is selected from the group consisting of multiwell plates, insert plates, columns, test tubes, and pipettes.

* * * * *